United States Patent [19]

Hashimoto et al.

[11] Patent Number: 4,772,594

[45] Date of Patent: Sep. 20, 1988

[54] PRODRUG COMPOUNDS, PROCESS FOR THE PREPARATION THEREOF AND SUSTAINED RELEASE PREPARATION COMPRISING THE SAME

[75] Inventors: Masashi Hashimoto, Ibaraki; Hidekazu Takeno, Nara; Hiroshi Kayakiri, Ibaraki; Akira Kagayama, Ibaraki; Yuji Tokunaga, Ibaraki; Tomoaki Iwasa, Ibaraki, all of Japan

[73] Assignee: Fujisawa Pharmaceutical Co., Ltd., Osaka, Japan

[21] Appl. No.: 26,530

[22] Filed: Mar. 16, 1987

[30] Foreign Application Priority Data

Mar. 14, 1986 [JP] Japan .................................. 61-57923

[51] Int. Cl.$^4$ ........................... A61K 31/56; C07J 9/00
[52] U.S. Cl. .................................. 514/178; 260/397.2
[58] Field of Search ....................... 514/182, 169, 178; 260/397.5, 397.2

[56] References Cited

FOREIGN PATENT DOCUMENTS 2028336 3/1980 United Kingdom .

OTHER PUBLICATIONS

Chemical Abstracts; vol. 93 (1980) #181439p; Slama et al.
Chemical and Pharmaceutical Bulletin, vol. 31, No. 11, Nov. 1983, pp. 4083–4090, Sasaki et al: Development of Lipophilic Prodrugs of Mitomycin C.III.
Chemical Abstracts, vol. 96, No. 17, Apr. 26, 1982, p. 793, Abstract No. 143180b.
Chemical Abstracts, vol. 93, No. 3, Jul. 21, 1980, p. 255, Abstract No. 21121a.

Primary Examiner—Leonard Schenkman
Assistant Examiner—Joseph A. Lipovsky
Attorney, Agent, or Firm—Oblon, Fisher, Spivak, McClelland & Maier

[57] ABSTRACT

The invention relates to a novel prodrug compound useful in the treatment of tumors, of the formula:

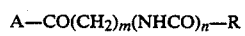

wherein
A is a residue of an antitumor substance having >NH or —NH$_2$ group in the molecule,
R is a residue of cholesterol,
m is an integer of 1 or 2 and
n is 0 or 1,
and its salts.

8 Claims, No Drawings

PRODRUG COMPOUNDS, PROCESS FOR THE PREPARATION THEREOF AND SUSTAINED RELEASE PREPARATION COMPRISING THE SAME

This invention relates to new pharmaceutical prodrug compounds, process for the preparation thereof and sustained release preparation comprising the same. As the object for sustained release of a drug in the body, so-called prodrugs have been developed by chemical modification of a drug molecule.

For example, the prodrug which is the combined form of 5-Fluorouracil

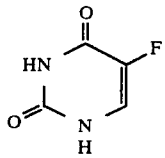

and cholesterol through the spacer [—CONH(CH$_2$)$_5$CO—]

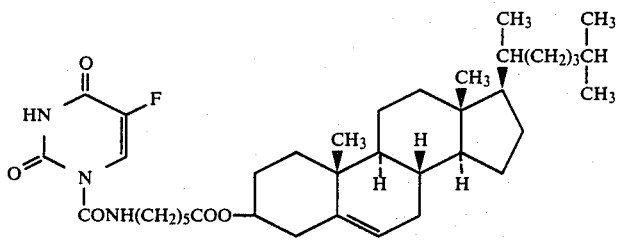

has been synthesized and the fact that the prodrug, which is entrapped in liposomes, could be gradually converted to the parent compound, 5-Fluorouracil in buffer solution is known.
(Proceedings of the 105th annual conference of pharmaceutical society of Japan (1985)
Title: Synthesis of 5-FU prodrugs having cholesterol moiety as a carrier and application of the prodrugs to lipid dispersion preparations).

Further the Mitomycin C derivative, cholesteryloxycarbonyl Mitomycin C,

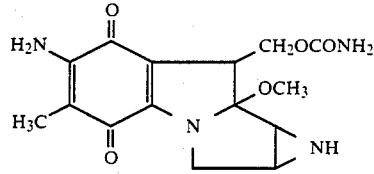

has been synthesized by coupling Mitomycin C to cholesteryl moiety through the spacer [—CO—].
[Chemical and Pharmaceutical Bulletin 31(11) 4083–4090,(1983)]

However, there were some problems: i.e. the above-mentioned Mitomycin C derivative could hardly be converted to the parent compound, Mitomycin C because of the stability of the linkage between Mitomycin C and cholesteryl moiety against chemical and enzymatic hydrolysis.

The inventors of this invention have carried out extensive studies in order to overcome the above-mentioned problems.

They have synthesized the derivatives of Mitomycin C by introducing steroid moiety through various kinds of new spacers, and have found that the prodrugs could be gradually converted to Mitomycin C, which is a parent compound, when the prodrugs were administered into the body. Further, they have prepared liposome preparations wherein the prodrugs were entrapped into liposomes, and have found that the entrapment of the derivative into liposomes decreased the conversion rate to Mitomycin C and the blood concentration of Mitomycin C was maintained for a long time and the toxicity was reduced when compared with that of the parent compound.

Further, they have found that the similar effects

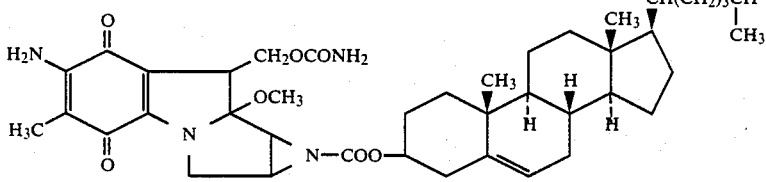

could be obtained when this invention was applied to 4-formyl-6,9-dihydroxy-14-oxa-1,11-diazatetracyclo-[7.4.1.0$^{2,7}$.0$^{10,12}$] tetradeca-2,4,6-trien-8-ylmethylcarbamate

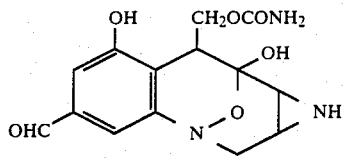

(hereinafter referred to as FR900482 substance) and bis(2-chloroethyl)amine

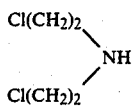

(hereinafter referred to as Nitrogen mustard), and the anti tumor activity was extensively improved in addition to the above-mentioned effects when this invention was applied to 1-β-D-arabinofuranosylcytosine

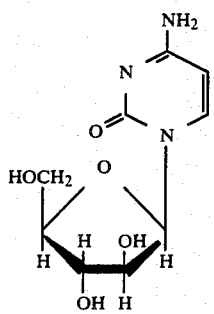

(hereinafter referred to as Cytarabine).

The prodrug compounds of this invention are new and represented by the following general formula [I]:

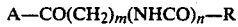

wherein,
is a residue of pharmaceutical compound having >NH or —NH₂ group in the molecule,
R is a residue of steroid compound,
m is an integer of 1 to 5 and
n is 0 or 1.

In the prodrug compounds [I], pharmaceutical compounds in the term "a residue of pharmaceutical compound having >NH group in the molecule" represented by A may be anti tumor substances [e.g. Mitomycin C, Nitrogen mustard, FR900482 substance, etc.].

Pharmaceutical compounds in the term "a residue of pharmaceutical compounds having —NH₂ group in the molecule" may be anti tumor substances [e.g. Cytarabine, Aminopterin, Azacitidine, Doxorubicin, Daunorubicin, etc.].

These residues of pharmaceutical compounds are intended to mean residues wherein a hydrogen atom is removed from >NH or —NH₂ group in the molecule of the pharmaceutical compounds.

The residue of steroid compound may be a group wherein a hydrogen atom is removed from hydroxy group at third position of steroid compound [e.g. cholesterol, chelestanol, lanosterol, ergosterol, lithocholic acid, etc.].

The prodrug compound [I] of this invention or its salt can be prepared by the following process.

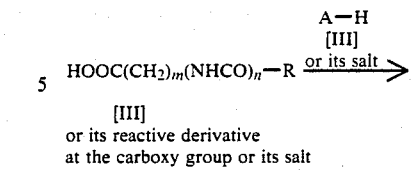

[II]
or its reactive derivative
at the carboxy group or its salt

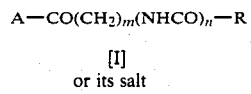

[I]
or its salt wherein A, R, m and n are each as defined above. Namely, the prodrug compound [I] or its salt can be prepared by reacting the compound [II] or its reactive derivative at the carboxy group or its salt with the compound [III] or its salt.

Suitable pharmaceutically acceptable salts of the compounds [I], [II] and [III] may include an acid addition salt such as an organic acid salt [e.g. acetate, maleate, tartrate, methanesulfonate, benzenesulfonate, toluenesulfonate, etc.] or an inorganic acid salt [e.g. hydrochloride, hydrobromide, sulfate, phosphate, etc.], a metal salt [e.g. sodium salt, potassium salt, calcium salt, magnesium salt, etc.], an ammonium salt, an organic amine salt [e.g. trimethylamine salt, triethylamine salt, dicyclohexylamine salt, etc.], and the like.

Suitable reactive derivative at the carboxy group of the compound [II] may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid or halogenated phosphoric acid), aliphatic carboxylic acid (e.g. pivalic acid or pentanoic acid), or aromatic carboxylic acid (e.g. benzoic acid); a symmetrical acid anhydride; an activated amide with imidazole, 4-substituted imidazole, dimethylpyrazole, triazole or tetrazole; or an activated ester (e.g. cyanomethyl ester or methoxymethyl ester) or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound [II] to be used.

The reaction is usually carried out in a conventional solvent such as water, methanol, ethanol, acetone, dioxane, acetonitrile, chloroform, methylene chloride, ethylene chloride, tetrahydrofuran, ethyl acetate, N,N-dimethyl formamide, pyridine or any other solvent which does not adversely influence to the reaction. These conventional solvents may be used in a mixture with water.

When the compound [II] is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, 1-ethyl-3-(3-dimethyl)carbodiimide hydrochloride, N,N-carbonylbis(2-methylimidazole), trialkyl phosphite, ethyl polyphosphate, phosphorus oxychloride (phosphoryl chloride), thionyl chloride, oxalyl chloride, 2-ethyl-7-hydroxybenzisoxazolium salt, 1-(p- chlorobenzenesulfonyloxy)-6-chloro-1H-benzotriazole, a Vilsmeier reagent which is, for example, prepared by the reaction of dimethylformamide with thionyl chloride, phosgen or oxalyl chloride, or the like.

The reaction may be also carried out in the presence of an inorganic or organic base such as an alkali metal bicarbonate, tri(lower)alkylamine (e.g. trimethylamine or triethylamine), pyridine, N-(lower)alkylmorphorine, N,N-di(lower)alkylbenzylamine, or the like. The reaction temperature is not critical, and the reaction is usually carried out under cooling or at room temperature.

It is to be noted that each of the object compound [I] and the starting compounds [II] and [III] may include one or more stereoisomers such as optical isomers or geometrical isomers due to asymmetric carbon atom or double bond in the molecule, and all of such isomers of the compounds [I], [II] and [III] are included within the scope of this invention.

The prodrug compound [I] of this invention or its salt is converted to the parent compound such as Mitomycin C, FR900482 substance, Nitrogen mustard or Cytarabine in blood, and all of these parent compounds have anti tumor activity and are useful for the treatment of various cancers (e.g. stomach cancer, lung cancer, lung adenocarcinoma, liver cancer, rectum cancer, pancreas cancer, breast carcinoma, hystero carcinoma, etc.) and leukemia (e.g. lymphocytic leukemia, myeloid leukemia, etc.), etc. The prodrug compound [I] of this invention can be prepared as an aqueous solution, an emulsion, a liposome suspension, etc. according to the conventional methods, and then these preparations are administered to the body, for example, by parenteral administration (e.g. intravenous injection, intramuscular injection, intratumor injection, rectal administration, etc.), oral administration, etc.

The prodrug compound thus administered is gradually converted to the parent compound (e.g. Mitomycin C, FR900482 substance, Nitrogen mustard or Cytarabine, etc.), and can maintain the concentration of the parent compound for a long time, improve the anti tumor effect, and reduce the toxicity when compared with the administration of the parent compound per se.

Among above-mentioned preparations, the most sustained blood concentration of the parent compound can be obtained when the prodrug compound is administered as a liposome suspension. Phospholipid to be used as film substance for preparing the liposome preparation may be phosphatidylcholine, phosphatidylethanolamine, phosphatidylinositol, phosphatidylserine, sphingomyelin etc., which are derived from egg, soybean or other animal tissue, egg yolk lecithin or soybean lecithin which are the mixture of the above-mentioned phospholipids, and synthetic lecithin such as dipalmitoyl lecithin, distearoyl lecithin etc. Conventional additives [e.g. cholesterols, dicetyl phosphate, α-tocopherol, etc.] may be optionally added to the phospholipids.

The liposomes can be prepared according to the conventional methods.

That is prodrug compound [I] or its salt and phospholipid(s) are dissolved in a suitable organic solvent such as chloroform methanol, ethanol, etc. and the solution is poured into a suitable container and is evaporated under reduced pressure. Then, surfactant (e.g. sodium cholate, etc.) and aqueous solution (e.g. phosphate buffered saline, etc.) are added to the residue and agitated. After the residue is dissolved, the surfactant is removed from this solution by a detergent removal apparatus to give the liposome preparation.

Another method is that phospholipid(s) is dissolved in organic solvent such as chloroform, ethanol, etc. and the solution is poured into a suitable container and is evaporated to give thin layer of phospholipid(s) under reduced pressure. Then, a solution of prodrug compound [I] or its salt is added thereto and shaked or sonicated. Liposomes can also be prepared by other conventional methods (e.g. ether injection method, etc.) and accordingly the method for preparing liposomes is not limited to the aforesaid methods.

Prodrug compound [I] of this invention or its salt may usually be administered with a unit dose of 1 mg to 1000 mg, 1 to 4 times a day.

However, the above dosage may be increased or decreased according to kinds of parent compound, age, weight and conditions of the patient or the administering method, or in combination with other anti tumor substances. In the case of parenteral administration, said dosage may be administered 1 to 2 times a week or with an interval of 1 to more than 2 weeks. To illustrate the effect of the present invention, test examples are shown in the following.

CONVERSION TEST 1

Chloroform solution containing egg yolk lecithin (84 μmole), egg yolk sphingomyelin (36 μmole) and Mitomycin C prodrug ( 6 μmole) obtained in the below-mentioned Example 1 or 2 was poured into a round-bottom flask and evaporated to dryness.

To this were added sodium cholate (258 mg) and pH 7.4 phosphate buffered saline (hereinafter referred to as PBS) (4.8 ml) and the mixture was agitated to give a clear purple solution.

Sodium cholate was removed from the solution by the Lipoprep dialyzer (detergent removal apparatus prepared by Diachema Co., Ltd.) to give a liposome suspension containing Mitomycin C prodrug.

Chloroform solution containing egg yolk lecithin (70 μmole), egg yolk sphingomyelin (30 μmole) and FR900482 substance prodrug (Example 6)(5 μmole) was poured into a round-bottom flask and a liposome suspension containing FR900482 substance prodrug was obtained in a similar manner to that of above-mentioned method.

Above-mentioned two liposome suspensions containing Mitomycin C prodrug were each diluted with PBS at 2.5 times.

The liposome suspension containing FR900482 substance prodrug was diluted with PBS to obtain the drug concentration of 0.5 μmole/ml and was filtered through millex-GV (trademark: prepared by Millipore Co., Ltd.) filter (0.22μ).

After the liposome suspension and ethanol solution of each prodrug (0.5 ml) were added to mouse, rat or human serum (4.5 ml, 37° C.), samples were taken periodically and the concentration of each prodrug was determined by high-performance liquid chromotography.

Conversion half lives (t ½) of each prodrug to each parent compound in various kinds of serum were calculated by the concentration of each prodrug remaining at each time.

TEST RESULT

Conversion on half lives (t ½) of each prodrug to each parent compound in various kinds of serum are shown in Table 1.

TABLE 1

| Test compound | Preparation | Half life (t ½) (hr) | | |
|---|---|---|---|---|
| | | Mouse | Rat | Human |
| Mitomycin C Prodrug (Example 1) | Ethanol Solution | — | 5.7 | 4.6 |
| | Liposome suspension | — | 10.0 | 7.1 |
| Mitomycin C Prodrug (Example 2) | Ethanol solution | — | 9.3 | 4.9 |
| | Liposome suspension | — | 17.3 | 10.1 |
| FR900482 Prodrug (Example 6) | Ethanol solution | 2.7 | 4.0 | 3.3 |
| | Liposome suspension | 4.6 | 10.3 | 9.9 |

From the above test result, it is found that the prodrugs of this invention can be converted to the parent compounds in blood in vitro and entrapment of each prodrug into liposomes increased its conversion half-life.

CONVERSION TEST 2

The mixture of chloroform and methanol (8:2 v/v) mixture containing egg yolk lecithin (70 μmole), egg yolk sphingomyelin (30 μmole) and Cytarabine prodrug (30 μmole) obtained in the below-mentioned Example 8 was poured into a round-bottom flask and evaporated to dryness. To this were added sodium cholate (53.8 mg) and PBS (5.0 ml) and the mixture was agitated to give a clear colorless solution.

Sodium cholate was removed from the solution by the Lipoprep dialyzer to give liposome suspension containing Cytarabine prodrug.

The liposome suspension was diluted with PBS to obtain the drug concentration of 5 μmole/ml and was filtered successively through polycarbonate membranes (prepared by Nuclepore Co., Ltd.) (0.2, 0.1 and 0.08μ respectively) and then filtered through a millex-GV filter (0.22 μ).

After the above-mentioned liposome suspension and ethanol solution of Cytarabine prodrug (0.08 ml) were added to rat serum (4.0 ml, 37° C.), samples were taken periodically and the concentration of Cytarabine prodrug was determined by high-performance liquid chromatography.

Conversion half lives (t ½) of the prodrug to the parent compound were calculated by the concentration of prodrug remaining at each time.

TEST RESULT

Conversion half lives (t ½) of the prodrug to the parent compound are shown in Table 2.

TABLE 2

| Test compound | Preparation | Half life (t ½) (hr) |
|---|---|---|
| Cytarabine Prodrug | Ethanol solution | 22.6 |

TABLE 2-continued

| Test compound | Preparation | Half life (t ½) (hr) |
|---|---|---|
| (Example 8) | Liposome suspension | 37.3 |

From the above test result, it is found that the prodrug of this invention can be converted to the parent compound in blood in vitro and entrapment of the prodrug into liposomes increased its conversion half-life.

BIOAVAILABILITY TEST 1

Chloroform solution (14.3 ml) containing egg yolk lecithin (126 μmole), egg yolk sphingomyelin (54 μmole) and Mitomycin C prodrug (Example 1) (24 μmole) was poured into a round-bottom flask and evaporated at one hour. To this were added sodium cholate (194 mg) and PBS (6 ml) and agitated. A liposome suspension containing Mitomycin C prodrug was obtained according to a similar manner to that of above-mentioned method. The liposome suspension thus prepared was diluted with PBS to obtain the drug concentration of 3.0 μmole/ml and was filtered through a polycarbonate membrane (0.1 μ). 1.0 ml of PBS solution of Mitomycin C or the liposome suspension containing Mitomycin C prodrug prepared by the above-mentioned method was administered intravenously to SD male rats (7 weeks, body weight: about 300 g, 4 per one group) and blood samples were withdrawn at appropriate intervals from subclavian vein. The plasma samples were deproteinzed and the concentration of Mitomycin C was determined by high-performance liquid chromatography.

While Mitomycin C prodrug in the blood was determined by high-performance liquid chromatography after extraction with ethanol from the freeze-dried blood samples.

TEST RESULT

The blood concentrations of Mitomycin C and Mitomycin C prodrug are shown in Table 3 as mean value ± standard deviation of four rats.

TABLE 3

| Preparation | Measured Compound | Blood concentration (nmole/ml) | | | | | | | |
|---|---|---|---|---|---|---|---|---|---|
| | | 5 min | 15 min | 30 min | 1 hr | 2 hr | 4 hr | 7 hr | 24 hr |
| PBS solution of Mitomycin C | Mitomycin C | 10.68 ± 1.45 | 5.54 ± 0.52 | 3.32 ± 0.64 | 1.04 ± 0.19 | 0.11 ± 0.06 | n.d. | n.d. | n.d. |
| Liposome suspension containing Mitomycin C | Mitomycin C | — | 1.38 ± 0.47 | 1.05 ± 0.15 | 0.87 ± 0.06 | 1.01 ± 0.12 | 0.96 ± 0.14 | 0.57 ± 0.12 | 0.04 ± 0.02 |
| Prodrug (Example 1) | Mitomycin C | — | 183.5 ± 31.1 | 174.6 ± 26.2 | 158.6 ± 14.6 | 112.9 ± 26.4 | 74.9 ± 15.6 | 52.1 ± 18.8 | 3.5 ± 1.8 |
| | Prodrug (Example 1) | | | | | | | | |

(n.d.: not detected)

From the above test results, it is found that the liposome suspension containing prodrug can maintain the concentration of the parent compound (Mitomycin C) for a long time.

BIOAVAILABILITY TEST 2

The liposome suspension containing Mitomycin C prodrug (Example 1), which was prepared in the above Bioavailability Test 1, was diluted with PBS at the concentration of Mitomycin C prodrug of 2.5 μmole/ml and was filtered through a polycarbonate membrane (0.1μ). 0.2 ml of PBS solution of Mitomycin C or the liposome suspension containing Mitomycin C prodrug was administered intravenously to ICR female mice (8 weeks, body weight: about 25 g, 3 per one group) respectively, and the blood samples were withdrawn by cardiac puncture under anesthesia. The blood concentrations of Mitomycin C and Mitomycin C prodrug were determined in accordance with the same procedures as described in Bioavailability Test 1.

TEST RESULT

The blood concentrations of Mitomycin C and Mitomycin C prodrug are shown in Table 4 as mean value ± standard deviation of three mice.

TABLE 4

| Preparation | Measured Compound | Blood concentration (nmole/ml) | | | | | | |
|---|---|---|---|---|---|---|---|---|
| | | 5 min | 15 min | 30 min | 1 hr | 2 hr | 4 hr | 7 hr |
| PBS solution of Mitomycin C | Mitomycin C | 9.15 ± 0.66 | 2.76 ± 0.26 | 1.57 ± 0.29 | 0.11 ± 0.20 | n.d. | n.d. | n.d. |
| Liposome suspension containing Mitomycin C | Mitomycin C | 1.33 ± 0.60 | 2.98 ± 2.13 | 1.16 ± 0.56 | 1.03 ± 0.40 | 1.15 ± 0.75 | 0.89 ± 0.24 | 0.57 ± 0.25 |
| Prodrug (Example 1) | Mitomycin C Prodrug (Example 1) | 239.8 ± 24.6 | 251.7 ± 1.1 | 211.0 ± 22.7 | 183.7 ± 27.2 | 137.1 ± 32.2 | 97.3 ± 13.4 | 42.1 ± 5.3 |

(n.d.: not detected)

From the above test result, it is found that the liposome suspension containing prodrug can maintain the blood concentration of the parent compound (Mitomycin C) for a long time.

BIOAVAILABILITY TEST 3

Each chloroform solution of Mitomycin C prodrug (Example 1) (4 μmole), Panacete 800 (trademark, prepared by Nihon Yushi Co., Ltd.) (40 mg), egg yolk lecithin (14 mg) and HCO-60 (trademark, prepared by Nikko Chemicals Co., Ltd.) (8 mg) was combined in a round-bottom flask and evaporated to dryness. To this was added PBS (1 ml) and emulsified with a sonicator to give an emulsion containing Mitomycin C prodrug. Each chloroform solution of liitomycin C prodrug (Example 1) (4 μmole) and HCO-60 (24 mg) was combined in a roundbottom flask and evaporated to dryness. The residue was dispersed in 1 ml of PBS and agitated vigorously to yield a clear solution. 0.2 ml of each preparations thus obtained which contained the prodrug at 4 μmole/ml, was administered to mice and the blood concentrations of Mitomycin C and Mitomycin C prodrug were determined according to the same procedures as described in Bioavailability Test 2.

TEST RESULT

The blood concentrations of Mitomycin C and Mitomycin C prodrug when two kinds of preparations containing Mitomycin C prodrug (Example 1) were administered intravenously to mouse are shown in Table 5 as mean value ± standard deviation of three mice.

TABLE 5

| Preparation | Measured Compound | Blood concentration (nmole/ml) | | | |
|---|---|---|---|---|---|
| | | 1 hr | 2 hr | 4 hr | 7 hr |
| Emulsion | Mitomycin C | 1.11 ± 0.67 | — | 0.26 ± 0.07 | 0.10 ± 0.02 |
| | Mitomycin C Prodrug (Example 1) | 250.7 ± 5.8 | — | 81.6 ± 6.1 | 39.0 ± 5.5 |
| Aqueous solution | Mitomycin C | 0.60 ± 0.09 | — | 0.18 ± 0.16 | 0.08 ± 0.03 |
| | Mitomycin C Prodrug (Example 1) | 185.5 ± 12.4 | — | 73.9 ± 13.9 | 22.2 ± 4.3 |

From the above test results, the emulsion and the aqueous solution of the prodrug can maintain the concentration of the parent compound (Mitomycin C) for a long time.

BIOAVAILABILITY TEST 4

The mixture of chloroform and methanol (8:2 V/V, 12 ml) containing egg yolk lecithin (147 μmole), egg yolk sphingomyelin (63 μmole) and Cytarabine prodrug (Example 8) (42 μmole) was poured into a round-bottom flask and evaporated at 37° C. for 10 minutes. To this were added sodium cholate (262.5 μmole) and PBS (7 ml) and agitated. A liposome suspension containing Cytarabine prodrug (concentration: 5 μmole/ml) was prepared according to a similar manner to that of above-mentioned method. The aqueous solution of Cytarabine or the liposome suspension containing Cytarabine prodrug prepared by the above-mentioned method (1.0 ml, each contained 5.0 μmole of drug/ml) was administered intravenously to SD male rat (7 weeks, body weight: about 250 g, 4 per one group) respectively, and blood samples were taken periodically from subclavian vein. The blood concentration of Cytarabine and Cytarabine prodrug were determined by high-performance liquid chromatography.

TEST RESULT

The blood concentrations of Cytarabine and Cytarabine prodrug are shown in Table 6 as mean value ± standard deviation of four rats.

TABLE 6

| Preparation | Measured Compound | Blood concentration (dose %/ml) | | | | | | | | |
|---|---|---|---|---|---|---|---|---|---|---|
| | | 5 min | 15 min | 30 min | 1 hr | 2 hr | 4 hr | 6 hr | 8 hr | 24 hr |
| Cytarabine solution | Cytarabine | 0.660 ± 0.054 | 0.578 ± 0.039 | 0.497 ± 0.029 | 0.356 ± 0.042 | 0.156 ± 0.020 | 0.026 ± 0.007 | n.d. | n.d. | n.d. |
| Liposome suspension containing Cytarabine Prodrug (Example 8) | Cytarabine | — | — | 0.027 ± 0.006 | 0.037 ± 0.018 | 0.058 ± 0.029 | 0.051 ± 0.008 | 0.057 ± 0.015 | 0.058 ± 0.015 | 0.048 ± 0.013 |
| | Cytarabine Prodrug (Example 8) | — | — | 6.30 ± 0.44 | 5.48 ± 0.50 | 4.93 ± 0.44 | 4.17 ± 0.36 | 3.48 ± 0.31 | 2.75 ± 0.23 | 0.67 ± 0.10 |

(n.d.: not detected)

From the above test result, it is found that the liposome suspension containing prodrug can maintain the blood concentration of the parent compound (Cytarabine) for a long time.

TOXICITY TEST

Each chloroform solution of egg yolk lecithin (126 μmole), egg yolk sphingomyelin (54 μmole) and Mitomycin C prodrug (Example 1) (3.75, 24 and 37.5 μmole respectively) was combined in a round-bottom flask and evaporated to dryness. Liposome suspensions containing Mitomycin C prodrug were obtained according to the same procedures as described above. The liposome suspensions were diluted with PBS to obtain the desired drug concentration (0.15, 0.96 and 1.50 mg/ml as Mitomycin C) and were filtered through polycarbonate membranes (0.1 μ). PBS solution of Mitomycin C (dose: 1.0 and 6.4 mg/kg/day respectively) or above-mentioned liposome suspension containing Mitomycin C prodrug (dose: 1.0, 6.4 and 10 mg/kg/day as Mitomycin C) were administered intravenously to ICR male mice (6 week) at Day 1, 3 and 5 and the body weight change was recorded from Day 1 to 15.

TEST RESULT

The body weight change when the each preparation was administered intravenously are shown in Table 7 as mean value ± standard deviation of five mice.

TABLE 7

| Preparation | Dose (mg/kg/day) | Body weight (g) 1 day | 5 days | 15 days |
| --- | --- | --- | --- | --- |
| PBS solution of Mitomycin C | 1.0 | 33.78 ± 0.82 | 33.86 ± 0.98 | 35.26 ± 1.05 |
|  | 6.4 | 35.54 ± 0.48 | 29.36 ± 0.48 | All died at 8 days |
| Liposome suspension containing Mitomycin C | 1.0 | 32.78 ± 1.22 | 33.04 ± 1.31 | 34.84 ± 1.63 |
|  | 6.4 | 33.86 ± 0.30 | 33.66 ± 0.67 | 35.50 ± 0.87 |
| Prodrug (Example 1) | 10.0 | 35.14 ± 0.43 | 34.52 ± 0.47 | 35.98 ± 0.48 |

From the test results, it is found that toxicity of the liposome suspension containing the prodrug is lower than that of the aqueous solution of the parent compound.

ANTI TUMOR TEST 1

The mixture of chloroform and methanol (8:2 V/V) containing egg yolk lecithin (245 μmole), egg yolk sphingomyelin (105 μmole) and Cytarabine prodrug (Example 8) (87.5 and 262.5 μmole respectively) was taken in a roundbottom flask. Liposome suspensions containing Cytarabine prodrug (Concentration: 10 and 20 μmole/ml respectively) were obtained in a similar manner to that of the above-mentioned method. Mouse leukemia cell L 1210 ($10^5$ cells) were implanted intraperitoneally into BDF female mice (7 weeks).

After 24 hours after inoculation, Cytarabine aqueous solution (dose: 1000 and 3000 μmole/kg respectively), above-mentioned liposome suspension containing Cytarabine prodrug (dose: 100 and 300 μmole/kg respectively) and aqueous solution of $N^4$-behenoyl-1-β-arabinofuranosylcytosine (hereinafter referred to as BHAC) which is a known compound as Cytarabine prodrug and is shown by the following structure (dose: 100 and 300 μmole/kg respectively) were administered intravenously to the mouse at a volume of 0.2 ml or 0.3 ml (in case the administration at the dose of 300 μmole/kg of Cytarabine prodrug) per 20 g of mouse body weight. After the treatment, survival of the mice was recorded.

BHAC:

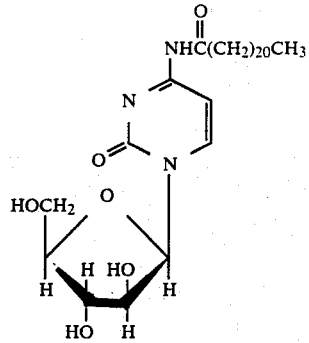

TEST RESULT

Mean survival times and percent of T/C, which was evaluated by the mean survival time of treated groups as compared to that of the control group when each preparation was administered intravenously are shown in Table 8.

TABLE 8

| Preparation | Dose (μmole/kg) | Mean survival time (days) | T/C (%) |
| --- | --- | --- | --- |
| Control | — | 9.0 ± 0.1 | — |
| Cytarabine aqueous solution | 100 | 9.5 ± 0.2 | 106 |
|  | 1000 | 10.8 ± 0.3 | 120 |
| BHAC aqueous solution | 100 | 11.0 ± 0.3 | 122 |
|  | 300 | 15.3 ± 0.5 | 170 |
| Liposome suspension containing Cytarabine Prodrug (Example 8) | 100 | 16.3 ± 0.3 | 181 |
|  | 300 | 33.3 ± 13.4 | 370 |

It is found that the anti tumor effect of the liposome suspension containing the prodrug of this invention was superior to that of the aqueous solution of the parent compound or BHAC.

ANTI TUMOR TEST 2

The mixture of chloroform and methanol (3:1 V/V) containing egg yolk lecithin (245 μmole), egg yolk sphingomyelin (105 μmole) and Cyarabine prodrug (Example 8) (87.5 and 157.5 μmole respectively) was taken in a round-bottom flask. Liposome suspensions containing Cytarabine prodrug (Concentration: 10 and 18 μmole/ml respectively) were obtained in a similar manner to that of the above-mentioned method.

A fragment of human lung adenocarcinoma A 549 was implanted under the subrenal capsule of BDF female mouse (8 weeks). Cytarabine aqueous solution (dose: 1000 μmole/kg) and above-mentioned liposome suspension containing Cytarabine prodrug (dose: 100 and 180 μmole/kg respectively) were administered intravenously to the mice at a volume of 0.2 ml per mouse body weight 20 g at Day 1, 5 and 9 after implantation. The tumor volume at Day 14 after implantation was measured and the growth inhibition percent was calculated. (In this test, to clarify the anti tumor effect of each preparation, 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as immunosuppressive substance(dose: 32 mg/kg) was administered subcutaneously at Day 1, 2, 5, 7, 9 and 12 after implanation.)

TEST RESULT

The tumor volume at Day 14 after implantation and the growth inhibition percent of tumor when each preparation was administered intravenously are shown in Table 9.

TABLE 9

| Preparation | Dose (μmole/kg) | Tumor volume (mm³) mean value ± standard error | Inhibition (%) |
|---|---|---|---|
| Control | — | 30.3 ± 6.9 | — |
| Cytarabine aqueous solution | 1000 | 17.7 ± 3.2 | 41.7 |
| Liposome preparation containing Cytarabine prodrug (Example 8) | 100 180 | 13.0 ± 3.0 5.5 ± 1.6 | 54.1 80.4 |

From the test results, it is found that the anti tumor effect of the liposome suspension containing the prodrug of this invention is superior to that of the aqueous solution of the parent compound.

The following Preparations and Examples are shown for the purpose of illustrating the present invention in more detail.

PREPARATION 1

To a suspension of glycine (1.50 g) in water (100 ml) was added triethylamine (4.04 g). Dioxane (200 ml) and cholesterol chlorocarbonate (8.98 g) were added to the resulting clear solution at 0° C. and the mixture was stirred for 3 hours. The reaction mixture was concentrated in vacuo and to the residue were added 1N-hydrochloric acid (23 ml) and chloroform (100 ml). Organic layer was separated, washed with water and dried over magnesium sulfate. Evaporation of the solvent gave crude crystal, which was washed with ethanol and collected by filtration to afford N-(cholest-5-en-β-oxycarbonyl)glycine (6.64 g) as a white crystal.

mp: 175°–177° C. (dec.)
IR (Nujol): 3320, 1750, 1665, 1570 cm⁻¹.

PREPARATION 2

To a solution of N-(cholest-5-en-3β-oxycarbonyl)glycine (2.92 g) in a mixture of dioxane (40 ml) and chloroform (6 ml) were added successively N-hydroxysuccinimide (0.69 g) and dicyclohexylcarbodiimide (1.236 g) at 0° C. and the reaction mixture was stood for 16 hours in a refrigerator. The resulting precipitate was collected by filtration and the filtrate was concentrated in vacuo to give succinimidyl N-(cholest5-en-3β-oxycarbonyl)-glycinate (3.23 g).

mp: 159°–164° C.
IR (CHCl₃) 3440, 1820, 1785, 1740, 1720 cm⁻¹.

PREPARATION 3

To a solution of β-alanine (56 mg) and sodium bicarbonate (84 mg) in water (10 ml) were added tetrahydrofuran (20 ml) and cholesterol chlorocarbonate (449 mg) at 0° C. The mixture was stirred for 1 hour. The reaction mixture was concentrated in vacuo and to the residue were added 0.1N hydrochloric acid (10 ml) and chloroform (40 ml). Organic layer was separated, washed with water and dried over magnesium sulfate. Evaporation of the solvent gave a crude product, which was dissolved in chloroform and applied to a silica gel column (40 g). Elution with a mixture of chloroform and methanol gave N-(cholest-5-en-3β-oxycarbonyl)-β-alanine (187 mg) as a white powder.

mp: 127°–130° C.
IR (CHCl₃): 3450, 1705 cm⁻¹.

PREPARATION 4

To a solution of 6-amino-n-caproic acid (131 mg) and sodium bicarbonate (84 mg) in a mixture of tetrahydrofuran (10 ml) and water (10 ml) were added tetrahydrofuran (10 ml) and cholesterol chlorocarbonate (449 mg) at 0° C. The mixture was treated in a similar manner to that of Preparation 3 to give N-(cholest-5-en-3β-oxycarbonyl)-6- amino-n-caproic acid (126 mg) as a white powder.

IR (CHCl₃): 3440, 1700 cm⁻¹.

EXAMPLE 1

To a solution of Mitomycin C (1.00 g) in N,N-dimethylformamide (20 ml) were added triethylamine (0.33 g) and succinimidyl N-(cholest-5-en-3β-oxycarbonyl)-glycinate (1.75 g) at room temperature and the reaction mixture was stirred for 4 hours at the same temperature. The solvent was evaporated off and to the residue was added chloroform and water. The organic layer was separated, washed with water and dried over magnesium sulfate. Evaporation of the solvent gave a crude product, which was dissolved in chloroform and applied to a silica gel column (50 g). Elution with chloroform gave [1aS-(1aα, 8β, 8aα, 8bα)]-6-amino-8-carbamoyloxymethyl-N'-[N-(cholest-5-en-3β-oxycarbonyl)glycyl]-1, 1a,2,8,8a,8b-hexahydro-8a-methoxy-5-methy-aziridino[2',3':3,4]pyrrolo [1,2-a]indole-4,7-dione (1.74 g) as a dark purple powder.

mp: >250° C.
Mass m/z 804 (M³⁰).

EXAMPLE 2

To a solution of cholest-5-en-3β-oxyacetic acid (667 mg), which was prepared according to the literature [Australian J. Chem., 24,143–51 (1971)], in chloroform (15 ml) were added N-hydroxysuccinimide (172 mg) and dicyclohexylcarbodiimide (324 mg) at 0° C. and the mixture was stirred overnight at room temperature. The precipitate was filtered off and the filtrate was concentrated in vacuo to give an active ester, which was used for the next reaction without further purification. To a solution of Mitomycin C (502 mg) in N,N-dimethylformamide (10 ml) were added active ester, triethylamine (152 mg) and 4-dimethylaminopyridine (20 mg). The reaction mixture was stirred overnight at 60° C. and concentrated in vacuo. To the residue were added chloroform and water. The organic layer was separated and dried over magnesium sulfate. Evaporation of the solvent gave a crude product, which was dissolved in a small amount of chloroform and applied to a silica gel column. Elution with chloroform gave [1aS-(1aα, 8β, 8aα,8bα)]-6-amino-8-carbamoyloxymethyl-N-(cholest-5-en-3β-oxyacetyl) 1,1a,2,8,8a,8b-hexahydro-8a-methoxy-5-methyl-aziridino [2',3':3,4]pyrrolo[1,2-a]indole-4,7-dione (695 mg) as a dark purple powder.

mp: 145°–150° C. (dec.).
IR (Nujol): 3430, 3320, 3200, 1710, 1650, 1600, 1550 cm⁻¹.

EXAMPLE 3

In a similar manner to that of Example 2, there was obtained [1aS-(1aα,8aβ,8bα)]-6-amino-8-carbamoyloxymethyl-N-(cholest-5-en-3α-oxyacetyl)-1,1a,2,8-,8a,8b-hexahydro-8a-methoxy-5-methyl-aziridino[2',3':3,4]pyrrolo[1,2-a]indole-4,7-dione, which is α-isomer of 3-position of cholesterol in Example 2.

mp: 118°–120° C.
IR (Nujol): 3420, 3320, 3200, 1700, 1600, 1550 cm$^{-1}$.

EXAMPLE 4

To a solution of N-(cholest-5-en-3β-oxycarbonyl)-β-alanine (56 mg) in a mixture of tetrahydrofuran (15 ml) and chloroform (5 ml) were added Mitomycin C (37 mg), triethylamine (13 mg) and 1-Ethyl-3-(3-dimethyl)-carbodiimide hydrochloride (24 mg). The reaction mixture was stirred overnight at room temperature and concentrated in vacuo. To the residue were added chloroform and water. The organic layer was separated and dried over magnesium sulfate. Evaporation of the solvent gave a crude product, which was dissolved in a small amount of chloroform and applied to a silica gel column. Elution with a mixture of chloroform and methanol gave [1aS-(1aα, 8β,8aα,8bα)]-6-amino-8-carbamoyloxymethyl-N'-[N-(cholest-5-en-3β-oxycarbonyl)-β-alanyl]-1,1a,2,8,8a,8b-hexahydro-8a-methoxy-5-methyl-aziridino[2',3':3,4]pyrrolo [1,2-a]indole-4,7-dione (22 mg) as a dark purple powder.

IR (CHCl$_3$) 3500, 3440, 3380, 1695, 1600, 1565 cm$^{-1}$.

EXAMPLE 5

To a solution of N-(cholest-5-en-3β-oxycarbonyl)-6-amino-n-caproic acid (63 mg) in a mixture of tetrahydrofuran (20 ml) and chloroform (5 ml) were added Mitomycin C (39 mg), triethylamine (13 mg) and 1-Ethyl-3-(3-dimethyl) carbodiimide hydrochloride (24 mg). The reaction mixture was stirred overnight at room temperature and concentrated in vacuo. To the residue were added chloroform and water. The organic layer was separated and dried over magnesium sulfate. Evaporation of the solvent gave a crude product, which was dissolved in a small amount of chloroform and applied to a silica gel column. Elution with a mixture of chloroform and methanol gave [1aS-(1aα,8β,8aα,8bα)]-6-amino-8-carbamoyloxymethyl-N'-[N-(cholest-5-en-3β-oxycarbonyl)-6-amino-n-caproyl]-1,1a,2,8,8a,8b-hexahydro-8a-methoxy-5-methylaziridino[2',3':3,4]pyrrolo[1,2-a]indole-4,7-dione (31 mg) as a dark purple powder.

IR (CHCl$_3$): 3500, 3440, 3370, 1700, 1600, 1560 cm$^{-1}$.

EXAMPLE 6

4-Formyl-6,9-dihydro-14-oxa-1,11-diazatetracyclo[7.4.1.0$^{2,7}$.0$^{10,12}$]tetradeca-2,4,6-triene-8-ylmethylcarbamate (32 mg) was dissolved in N,N-dimethylformamide (1.0 ml). To the solution was added triethylamine (14 μl) and succinimidyl N-(cholest-5-en-3β-oxycarbonyl)glycinate (60 mg). The mixture was stirred for 6 hours at ambient temperature and evaporated in vacuo. The residue was subjected to a preparative thin layer chromatography, developing with a mixture of chloroform and methanol to afford 2 isomers at C-9 of 11-[N-(cholest-5-en-3β-oxycarbonyl)glycyl]-4-formyl-6,9-dihydroxy-14-oxa-1,11-diazatetracyclo[7.4.1.0$^{2,7}$.0$^{10,12}$]tetradeca-2,4,6-triene-8-ylmethylcarbamate (9-α-OH isomer 31 mg and 9-β-OH isomer 15 mg).

mp: 168°–170° C. (dec.) (a mixture of 9-α-OH isomer and 9-β-OH isomer).

9α-OH isomer
IR (CHCl$_3$): 3340, 2950, 1695, 1586, 1355 cm$^{-1}$.
SIMS: 791 [M+H]$^+$, 813 [M+Na]$^+$.

9β-OH isomer
IR (CHCl$_3$): 3340, 2945, 1695, 1583, 1350 cm$^{-1}$.
SIMS: 791 [M+H]$^+$, 829 [M+K]$^+$.

EXAMPLE 7

To bis(2-chloroethyl)amine hydrochloride (1.347 g) in 25% sodium hydroxide solution (100 ml) was added methylene chloride (100 ml) and the mixture was shaked. Organic layer was separated and dried with potassium carbonate and filtered. Methylene chloride was evaporated under reduced pressure to obtain bis(2-chloroethyl)amine (0.52 g) as an oily substance.

To a solution of N-(cholest-5-en-3β-oxycarbonyl)glycine (160.8 mg) in dry tetrahydrofuran (50 ml) was added said bis(2-chloroethyl)amine (85.2 mg) and dicyclohexylcarbodiimide (61.9 mg) at 0° C. under blowing nitrogen gas and the mixture was stirred for 6 hours. After standing overnight (17 hours) at refrigerator, the reaction mixture was filtered and the solvent was evaporated under reduced pressure. The residue was solved in a mixture of chloroform and methanol (50:1) and was subjected to preparation column chromatography (PLC) eluting with a mixture of chloroform and methanol (50:1). The desired parts were gathered, extracted with a mixture of chloroform and methanol (4:1), filtered and concentrated under reduced pressure to give N-[N-(cholest-5-en-3β-oxycarbonyl)glycyl]bis(2-chloroethyl)amine (110 mg).

mp: 98°–100° C.

EXAMPLE 8

To a solution of N-(cholest-5-en-3β-oxycarbonyl)glycine (2.74 g) and triethylamine (0.78 ml) in tetrahydrofuran (40 ml) was added dropwise ethyl chlorocarbonate (0.61 g) at −15° C., and the reaction mixture was stirred for 20 minutes at −15° C. To the reaction mixture a solution of 1-β-D-arabinofuranosylcytosine (1.37 g) in dimethylformamide (30 ml) was added dropwise at −15° C. to −10° C. After the addition, the mixture was stirred for one hour at 5° C. and then for 30 minutes at room temperature. The reaction mixture was concentrated in vacuo. The residue was washed with methanol and dried to afford a crude reaction product, which was purified by silica gel column chromatography to yield N$^4$-[N-(cholest-5-en-3β-oxycarbonyl)glycyl]-1-β-D-arabinofuranosylcytosine (1.8 g) as a white powder.

mp: 159°–161° C. (dec.)
IR (Nujol): 3330, 2850, 1690, 1640, 1570 cm$^{-1}$.
SIMS (m/z): 713 [M+H]$^+$, 751 [M+K]$^{30}$.

What we claim is:

1. A Prodrug compound of the formula:

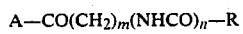

A—CO(CH$_2$)$_m$(NHCO)$_n$—R wherein
A is a residue of an antitumor substance having >NH or —NH$_2$ group in the molecule,
R is a residue of cholesterol,
m is an integer of 1 or 2 and
n is 0 or 1,
and its salts.

2. A Prodrug compound according to claim 1, wherein the antitumor substance is Mitomycin C.

3. A Prodrug compound according to claim 1, wherein the antitumor substance is Nitrogen mustard.

4. A Prodrug compound accoridng to claim 1, wherein the antitumor substance is FR 900482 substance.

5. A Prodrug compound according to claim 1, wherein the antitumor substance is Cytarabine.

6. A sustained release antitumor preparation comprising, as an active ingredient, an effective amount of a Prodrug compound of claim 1 or its salts thereof in association with pharmaceutically acceptable carrier or excipient.

7. A method for treating tumor in a patient comprising administering an effective amount of a Prodrug compound of claim 1 to said patient.

8. A process for preparing a Prodrug compound of the formula:

$$A-CO(CH_2)_m(NHCO)_n-R$$

wherein
A is a residue of an antitumor substance having $>$NH or $-NH_2$ group in the molecule,
R is a residue of cholesterol,
m is an integer of 1 or 2 and
n is 0 or 1,
or its salt, which comprises
reacting a compound of the formula:

$$HOOC(CH_2)_m(NHCO)_n-R$$

wherein R, m and n are each as defined above, or its reactive derivative at the carboxy group or it salt, with a compound of the formula:

$$A-H$$

wherein A is as defined above, or its salt.

* * * * *